United States Patent
Katsigras et al.

(10) Patent No.: US 7,008,600 B2
(45) Date of Patent: *Mar. 7, 2006

(54) DISINFECTING ARTICLE AND CLEANING COMPOSITION WITH EXTENDED STABILITY

(75) Inventors: George Katsigras, Pleasanton, CA (US); Surinder Bains, Pleasanton, CA (US); Lily Cheng, Pleasanton, CA (US); Thomas W. Kaaret, Pleasanton, CA (US); William L. Smith, Pleasanton, CA (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/870,093

(22) Filed: Jun. 16, 2004

(65) Prior Publication Data

US 2005/0025668 A1 Feb. 3, 2005

Related U.S. Application Data

(63) Continuation-in-part of application No. 10/632,573, filed on Aug. 1, 2003.

(51) Int. Cl.
*A61L 2/00* (2006.01)
*A01N 59/08* (2006.01)

(52) U.S. Cl. .............. 422/292; 422/1; 422/37; 422/40; 424/443; 424/661

(58) Field of Classification Search ............ 422/1, 422/37, 40, 292; 424/404, 402, 661, 443; 428/198
See application file for complete search history.

(56) References Cited

U.S. PATENT DOCUMENTS

| | | | | |
|---|---|---|---|---|
| 4,998,984 | A | 3/1991 | McClendon | 206/205 |
| 5,087,450 | A | 2/1992 | Lister | 424/402 |
| 5,786,065 | A * | 7/1998 | Annis et al. | 428/141 |
| 5,811,113 | A | 9/1998 | Dorr et al. | 424/404 |
| 5,985,302 | A | 11/1999 | Dorr et al. | 424/404 |
| 6,231,747 | B1 | 5/2001 | Fukuzuka et al. | 205/500 |
| 6,313,049 | B1 | 11/2001 | Heady et al. | 442/123 |
| 6,361,784 | B1 * | 3/2002 | Brennan et al. | 424/402 |
| 6,387,384 | B1 | 5/2002 | Probert et al. | 424/404 |
| 6,423,804 | B1 * | 7/2002 | Chang et al. | 526/319 |
| 2002/0106478 | A1 | 8/2002 | Hayase et al. | 428/91 |

FOREIGN PATENT DOCUMENTS

| | | |
|---|---|---|
| WO | WO 99/52360 | 10/1999 |
| WO | WO 01/92622 | 12/2001 |

* cited by examiner

*Primary Examiner*—Krisanne Jastrzab
(74) *Attorney, Agent, or Firm*—David Peterson

(57) ABSTRACT

The present invention relates to a disinfecting article, a sealable housing system for disinfecting articles, and a disinfecting composition comprising a hypohalite composition and a surfactant, for cleaning and disinfecting surfaces, with improved stability and extended efficacy for cleaning and disinfecting surfaces with residues such as foods, dirt, microorganisms and many other common contaminates. The disinfecting article is preferably a wipe that is comprised of high denier fibers and stored in a sealable housing system to ensure the stability of the substrate in the hypohalite releasing solution.

24 Claims, 1 Drawing Sheet

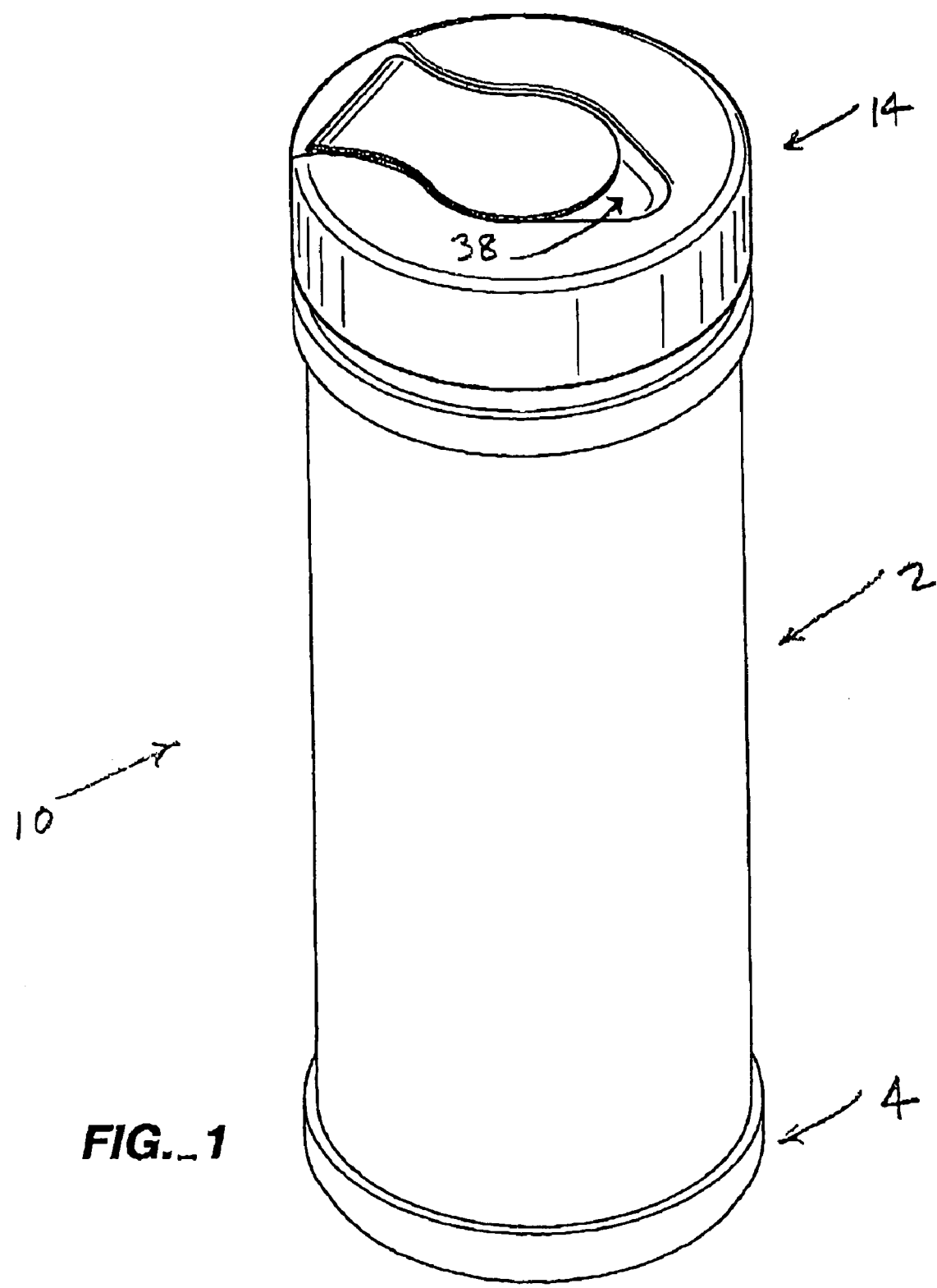
FIG._1

DISINFECTING ARTICLE AND CLEANING COMPOSITION WITH EXTENDED STABILITY

CROSS REFERENCE TO RELATED APPLICATION

The present application is a continuation-in-part of Co-pending application Ser. No. 10/632,573, which was filed Aug. 1, 2003, entitled "DISINFECTING ARTICLE WITH EXTENDED EFFICACY", and incorporated herein.

FIELD OF THE INVENTION

The present invention relates to disinfecting articles providing effective cleaning and antimicrobial treatment of microbiologically contaminated surfaces. More particularly, it relates to the use of sealable housings and aqueous hypohalite compositions associated with a hypohalite stable and hypohalite non-degrading absorbent substrate that preserves the antimicrobial efficacy of the disinfectant article over representative storage conditions.

BACKGROUND OF THE INVENTION

There is a need for a stable cleaning and disinfecting wipe and article that is capable of cleaning and removing residues from soiled surfaces while simultaneously destroying undesirable microorganisms, e.g. bacteria, mold, viruses, prions and the like that colonize on common surfaces with which people come into contact, such as door knobs, countertops, toilet seats, floors, beds, walls, and the like.

Hypohalite releasing compounds, such as the hypohalites and related compounds that release active forms of hypohalite and/or halogens, are extremely effective disinfectants capable of destroying a wide range of microorganisms. Hypohalite releasing antimicrobial compounds, and in particular the hypohalites, constitute a class of strong chemical oxidants possessing both cleaning and bleaching properties in addition to their antimicrobial properties making them superior to other disinfectants, such as quaternary ammonium biocides. The hypohalite class of chemical oxidants act to rapidly oxidize susceptible substances found in inorganic, organic and biological materials, rendering them more easily removed from surfaces, and in the case of colored or pigmented materials, bleaching them to white or colorless end products resulting in effective cleaning and stain removal from soiled surfaces. Owing to their strong oxidizing capability, hypohalites also posses inherent disinfection properties and additionally possess desirable characteristics including excellent aqueous solubility, mobility and a highly dissociative ionic nature. A further advantage of the hypohalite class with regard to disinfectancy, is the speed and efficacy with which they attack microorganisms and either destroy them or render them non-viable following very short contact times. Yet a further advantage of the hypohalites is the wide susceptibility of many different types of microbial pests to their strong oxidizing potential and essentially the absence of any known microbe to develop an effective resistance against the action of these materials.

Typically, microbiologically contaminated surfaces seldom comprise only the microorganisms themselves, but include the presence of soils and other residues, including organic, inorganic and biological residues associated with the source of the microbiological contamination. These residues, including, for example, saliva, bodily is fluids, blood and common soils such as foods, oils and dirt, not only host microorganisms, but can act to shield and protect the microorganisms from the disinfectant action of non-hypohalite disinfectant materials.

One seeming disadvantage of the hypohalite class of materials is their susceptibility to decomposition, including self-decomposition and reactive decomposition owing to the interaction of the hypohalites with the substrates and materials, which they contact during packaging and storage. Particularly in the case of pre-wetted wipes, the disinfecting hypohalite composition is impregnated onto and interacts with the absorbent carrier substrate during storage. Hence, freshly prepared solutions or disinfectant articles utilizing these materials are typically required to ensure adequate activity for ensuring effective disinfection of surfaces. Attempts have been made in the past to provide a convenient disinfectant article by absorbing a hypohalite solution onto an absorbent towel or carrier. However, prior attempts have failed to produce a hypohalite releasing disinfectant wipe with sufficient stability to ensure suitable disinfecting efficacy at time of use, particularly following typical storage times and/or less than ideal storage conditions representative of real world environments encountered in the home, office, business, hospital or field where needed.

U.S. Pat. No. 4,998,984, to McClendon, describes a premoistened disinfectant article impregnated with a disinfectant composition that may include sodium hypochlorite and is prepackaged in a liquid impermeable container. U.S. Pat. No. 5,087,450, to Lister, describes a viral wipe to remove organic material having viral contaminants from a surface which consists of a porous gauze pad lined with a non-porous flexible fluid impervious barrier layer fused to one side and impregnated with 10% sodium hypochlorite and stored in a protective foil, plastic and paper layered package. Lister notes that the 10% sodium hypochlorite solution becomes unstable within a short period of time.

U.S. Pat. No. 5,985,302, to Dorr, et al., describes a method for inactivating HIV infected blood which involves first swabbing a contaminated surface with a first aqueous calcium and/or sodium hypochlorite impregnated fibrous towelette, followed by a second swabbing with a second towelette impregnated with a neutralizing sodium thiosulfate solution. However, the Dorr, et al. example exhibits poor stability and complete loss of disinfectant power even of a dry calcium hypochlorite/methyl cellulose system freshly dissolved in water to produce a disinfecting solution after only 10 days storage at 50° C. U.S. Pat. No. 6,313,049, to Heady, describes a pre-packaged fabric-saturated absorbent sheet with the U.S. food-industry legal chlorine disinfectant solution and discloses the use of cotton, paper or sponge sheets as absorbents. U.S. Pat. No. 6,387,384, to Probert, describes a prepackaged towelette bearing sodium hypochlorite and discloses the use of gauze or bandage material as absorbents.

The prior art fails to provide a stable disinfectant article that maintains acceptable stability after storage times and storage conditions typical of actual usage conditions encountered in the real world. For instance, most commercial product distribution channels result in products ageing several months following manufacture before being placed on sale, followed by significant delays before actually being used. During this time, products are seldom stored under ideal conditions, but rather are exposed to temperature variations typical of the home, field and industrial environment. Most significantly, the prior art fails to disclose suitable absorbent carrier substrates with acceptable stability or a reliable means for selecting an appropriate absorbent material suitable for extended stability of aqueous hypohalite disinfectant articles to ensure reliable antimicrobial efficacy when needed.

Clearly, there remains an unmet need for an aqueous hypohalite disinfecting article with improved stability that can provide the required antimicrobial efficacy for disinfecting microbiologically contaminated surfaces, particularly following typical storage times and/or less than ideal storage conditions representative of real world environments encountered in the home, office, business, hospital or field where needed.

SUMMARY OF THE INVENTION

The present invention relates to a disinfecting article, a housing system for disinfecting articles, and disinfecting composition, for cleaning and disinfecting surfaces, with improved stability and extended efficacy for cleaning and disinfecting surfaces with residues such as foods, dirt, microorganisms and many other common contaminates. The disinfecting article is preferably a wipe. In one embodiment of the invention, the disinfecting article comprises an aqueous hypohalite releasing composition and an absorbent carrier containing said aqueous hypohalite releasing composition, wherein said absorbent carrier comprises fibers having a denier of 1.5 or greater. In another aspect of the invention, the disinfecting article comprises an aqueous hypohalite releasing composition comprising a surfactant and an absorbent carrier containing said aqueous hypohalite releasing composition. In another aspect of the invention, the housing system for disinfecting articles comprises a disinfecting article comprising an aqueous hypohalite releasing composition and an absorbent carrier containing the aqueous hypohalite releasing composition, and a sealable container for storing and dispensing said disinfecting article.

The disinfectant articles provide a sufficient amount of active hypohalite which remains effective for an extended period of time to reliably disinfect hard surfaces such as countertops, toilet seats, door knobs and the like commonly found in the home, hospital, food service and other industries.

DETAILED DESCRIPTION OF THE INVENTION

Before describing the present invention in detail, it is to be understood that this invention is not limited to particularly exemplified systems or process parameters as such may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "surfactant" includes two or more such surfactants.

Unless otherwise defined, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The following examples illustrate disinfecting articles and compositions of the described invention. The exemplified compositions and articles are illustrative only and do not limit the scope of the invention. Unless otherwise specified, the proportions in the examples and elsewhere in the specification are by weight percent of the total liquid composition, and loading ratios of the example compositions are by unit weight of composition per unit weight of the absorbent carrier matrix and thus expressed as a unit-less weight/weight ratio.

As used herein, the term "disinfect" shall mean the elimination of many or all pathogenic microorganisms on the surface with the exception of bacterial endospores. As used herein, the term "sanitize" shall mean the reduction of contaminants on the device surface to levels considered safe according to public health ordinance, or that reduces the bacterial population by significant numbers where public health requirements have not been established. And at least 99% reduction in bacterial population within a 24 hour time period is deemed "significant." As used herein, the term "sterilize" shall mean the complete elimination or destruction of all forms of microbial life.

The present invention relates to a disinfecting article, housing system and disinfecting composition for cleaning and disinfecting surfaces, in which the disinfecting article comprises an aqueous hypohalite releasing composition adsorbed onto an absorbent carrier material. The disinfecting articles comprise an aqueous hypohalite releasing composition and an absorbent carrier comprising a substrate. The present invention also relates to a housing system for storing and dispensing a single or multiple number of disinfectant substrates.

Absorbent Carrier

Suitable absorbent carriers may be provided by a variety of sources, including woven and non-woven webs, fabrics, foams, sponges and similar material constructs capable of absorbing the liquid disinfectant composition of the present invention. In one embodiment, the absorbent carriers have a series of apertures, which improve substrate stability, because apertures can decrease the overall surface area by up to 20%. Generally, the absorbent carrier is preferred to be in sheet form. Preferably, the cross-sectional thickness dimension of the absorbent carrier sheet is proportionally smaller than either its approximate width or length dimension in order to provide at least one surface whose surface area is sized appropriately with respect to the intended surface to be treated with the disinfectant article. The absorbent carrier may be formed into individual sheets or wipes or as a continuous sheet. In continuous sheet form, it is preferred to provide means, such as partial tears or perforations across at least one dimension of the sheet, such that the continuous sheet may be subdivided prior to use to a suitable size for the particular need at hand.

The absorbent carrier may comprise a wipe or cleaning pad. The wipe or cleaning pad can be used with the hand, or as part of a cleaning implement attached to a tool or motorized tool, such as one having a handle. Examples of tools using a wipe or pad include U.S. Pat. No. 6,611,986 to Seals, WO00/71012 to Belt et al., U.S. Pat. App. 2002/0129835 to Pieroni and Foley, and WO00/27271 to Policicchio et al.

The absorbent carrier may comprise a single layer or multiple layers of one or more materials. The absorbent carrier may also comprise a combination of one or more materials and/or one or more forms of materials. The multiple layers or multiple forms of materials are bonded to each other by suitable means to prevent separation. For example, a sheet of one material may be combined with a second sheet of a second material and bonded together by suitable means. Suitable means of bonding sheets together includes, by way of example and not by way of limitation, adhesion and heat or sonic welding. A further example, a non-woven sheet of one material may be combined with a second material formed into deformable and compressible foam, and bound together by a suitable means. In this manner, all conceivable combinations of materials may be combined to provide useful articles for a variety of cleaning and disinfecting requirements.

Further, the absorbent carrier can be combined with non-absorbent materials, preferably in the form of films, sheets or blocks. Preferably, the non-absorbent materials are liquid impervious, in that they do not permit the passage of the disinfectant compositions of the present invention. In one example, the non-absorbent materials may be bonded to one side of a suitable absorbent carrier creating a layered disinfectant article. The layered disinfectant article has a liquid impervious barrier to prevent passage of the disinfectant composition from the absorbent material to the outside surface of the barrier material. Thus the liquid impervious barrier allows the user to handle the layered disinfectant article without direct contact with the disinfectant wetted side of the layered article. Another example is a thin liquid impervious plastic sheet bounded to an absorbent foam, whereby the user contacts the plastic sheet during use rather than contacting the liquid disinfectant that is absorbed into the foam and that is displaced by pressure applied while wiping the surface to be treated.

According to the present invention, the absorbent carrier may be produced by any method known in the art. For example, non-woven material substrates can be manufactured by dry forming techniques such as air laying or wet laying such as on a paper making machine. Other non-woven manufacturing techniques, such as hydroentangling, melt blown, spun bonded, needle punched and related methods may also be used. However, it is preferred that the substrate be made substantially free of binder or latex and other impurities that may degrade or interact with the disinfectant composition. Thus, many manufacturing techniques, such as air laying, are not preferred because they do not lend themselves to the formation of binder-free and latex-free absorbent carriers. Hydroentrangling manufacturing techniques using high speed water jets are generally preferred due to the high density matrices produced and the high degree of cleanliness of the resulting non-woven articles produced by this method.

Suitable absorbent carriers are generally selected from man-made and synthetic construction materials or substrates, preferably including synthetic polymers. For good cleaning, absorption, handling and loading characteristics, it is desirable that the absorbent carrier materials be in the form of fiber, webs or foams of the suitable construction materials.

Suitable forms of employing fibers include woven and non-woven structures. Suitable woven structures include, by way of example and not by way of limitation, meshes, screens, knits, fabrics and other similarly woven structures, of sufficiently high fiber count and strength to be handled by typical machinery and process equipment needed for forming, cutting and packaging the disinfectant articles, preferably when in a dry state. Suitable woven structures include those structures that are of sufficiently high fiber count and strength to be dispensed and handled during use, preferably when in a dry state, and more preferably when in a wetted state.

Suitable woven and non-woven structures are composed of fibers with both sufficient fiber sizes and fiber densities to provide some absorption capacity and enable loading of a sufficient quantity of the disinfectant solution so as to provide for effective treatment of surfaces. The standard fiber size is 1 denier or 1 D. Fibers with a larger than standard denier size are preferable because they can improve the stability of the substrates which makes them effective for a longer period of time. Most preferably, the fibers in the substrate will have about 1.5 to 6.0 denier. Denier is a weight-per-unit-length measurement of a linear material defined as the number of grams per 9000 meters. Suitable non-woven structures include those structures that are of sufficiently high fiber count and strength to be dispensed from the packaging articles, without significant deformation, tearing or ripping, and handled during use, without unraveling, abrading or tearing, preferably when in a wetted state.

The nonwoven substrate may comprise apertures. The apertures may be formed by the PUB pattern, which is described in U.S. Pat. No. 5,858,515 to Stokes et al, the entire contents of which are hereby incorporated by reference. Apertured structures also include apertured films as described in U.S. Pat. No. 6,635,799 to Osborn et al.

Absorbent Carrier Substrates

Suitable substrates employed for constructing the absorbent carrier may be provided by a variety of sources, and include all suitable substrates that are hypohalite stable, in that they undergo no significant degradation. That is, suitable substrates that undergo no significant chemical or physical change in structure, properties or form, owing to contact with the disinfectant compositions employed in the present invention, even after extending contact or storage times under representative storage conditions. Preferred are suitable substrates that do not cause significant degradation of the associated or absorbed disinfecting compositions, that is, substrates that do not catalyze or significantly accelerate the decomposition of the associated hypohalite compositions.

Suitable materials of construction generally include synthetic polymer substrates, such as, by way of example and not by way of limitation, polyethylene terephthalate (PET), polyester (PE), high density polyethylene (HDPE), polyvinyl chloride (PVC), chlorinated polyvinylidene chloride (CPVC), polyacrylamide (ACAM), polystyrene (PS), polypropylene (PP), polycarbonate (PC), polyaryletherketone (PAEK), poly(cyclohexylene dimethylene cyclohexanedicarboxylate) (PCCE), poly(cyclohexylene dimethylene terephthalate) (PCTA), poly(cyclohexylene dimethylene terephtalate) glycol (PCTG), polyetherimide (PEI), polyethersulfone (PES), poly(ethylene terephthalate) glycol (PETG), polyketone (PK), poly(oxymethylene); polyformaldehyde (POMF), poly(phenylene ether) (PPE), poly(phenylene sulfide) (PPS), poly(phenylene sulfone) (PPSU), syndiotactic polystyrene (syn-PS), polysulfone (PSU), polytetrafluoroethylene (PTFE), polyurethane (PUR), poly(vinylidene fluoride) (PVDF), polyamide thermoplastic elastomer (TPA), polybutylene (PB), polybutylene terephthalate (PBT), polypropylene terephthalate (PPT), polyethylene naphthalate (PEN), polyhydroxyalkanoate (PHA), poly(methyl)methacrylate (PMMA) and polytrimethylene terephthalate (PTT).

Suitable materials of construction also include copolymers made from the following monomers: acrylonitrile-butadiene-styrene (ABS), acrylonitrile-styrene-acrylate (ASA), ethylene-propylene (E/P), ethylene-vinyl acetate (EVAC), methyl methacrylate-acrylonitrile-butadiene-styrene (MABS), methacrylate-butadiene-styrene (MBS), melamine-formaldehyde (MF), melamine-phenol-formaldehyde (MPF), phenol-formaldehyde (PF), styrene-butadiene (SB), styrene-maleic anhydride (SMAH), copolyester thermoplastic elastomer (TPC), olefinic thermoplastic elastomer (TPO), styrenic thermoplastic elastomer (TPS), urethane thermoplastic elastomer (TPU), thermoplastic rubber vulcanisate (TPV), copolymer resins of styrene and acrylonitrile (SAN), styrene butadiene copolymer (SBC) and vinyl acetate-ethylene copolymer (VAE).

Preferably, the substrate is a blend of polypropylene and polyethylene terephthalate. The ratio may vary, but a preferred ratio is 50% polypropylene to 50% polyethylene terephthalate and a more preferred ratio is 20% polypropylene to 80% polyethylene terephthalate.

The substrate and the absorbent carrier constructed from said substrate herein is substantially free, preferably devoid, of any binders or latex materials. Substantial elimination of binders and latexes, and the like, can be accomplished by pre-washing the dry absorbent carrier in soft, distilled or de-ionized water or other solvents, or by using a substantially binder-free and latex-free process, such as hydroentangling (also known in the art as spunlace technology). More specifically, in the hydroentangling process, a fibrous web is subjected to high-velocity water jets, preferably employing de-ionized, distilled or soft water that entangle the fibers. The non-woven material may then be subjected to conventional drying and wind-up operations, as known to those skilled in the art. Since the hydroentangling process precludes the use of binders, and can be used to wash off fiber latexes, it is on of the most preferred processes for use in the manufacture of materials of construction of the present invention. Suitable materials of construction that are readily available in commerce include the SONTARA® brand of non-woven fabrics produced by Dupont. Representative materials include 100% polyester substrate materials designated SONTARA® 8001, 8005H, 8010 and 8061, and 50% polyester/50% Dacron® blends designated SONTARA® 8100 and including hydrophilically modified 100% polyester substate material designated SONTARA® 8005H. Additional examples include materials commercially available from Polymer Group Inc, including 100% spunlaced polyester and polypropylene materials designated M001, M022, M040X, CG003, CG005, CG2009, M017, N2006 and T133. Representative materials also include spunlaced 100% polyester materials, designated as 350160 and 10203-003, available from Jacob Holms Industries.

Absorbency and Loading

The absorbent carrier preferably has a weight of from about 10 g/m² (grams per meter squared) to about 200 g/m². More preferably, the absorbent carrier has a weight of at least about 15 g/m² and more preferably less than about 150 g/m², more preferably the weight is in the range of about 20 g/m² to about 120 g/m², and most preferably from about 25 g/m² to about 100 g/m².

In preparing pre-wetted disinfectant articles according to the present invention, the composition is applied to at least one surface of the absorbent carrier material. The composition can be applied at any time during the manufacture of the articles. Preferably the composition is applied to the absorbent carrier after the absorbent carrier has been dried. Any variety of application methods that evenly distribute disinfecting compositions can be used. Suitable methods include, for example, spraying, dipping, or rolling, whereby the composition is forced through tubes in contact with the absorbent carrier whilst the absorbent carrier passes across the tube. Combinations of these application techniques may also be used, for example, spraying the composition on a rotating surface, such as calender roll, which then transfers the composition to the surface of the absorbent carrier. The composition can be applied either to one surface of the absorbent carrier or both surfaces, and preferably both surfaces.

The composition can also be applied uniformly or non-uniformly to the surfaces of the absorbent carrier. By non-uniform it is meant that, for example, the amount or pattern of distribution of the composition can vary over the surface of the absorbent carrier. That is, some of the surface of the absorbent carrier can have greater or lesser amounts of disinfectant composition, including portions of the surface to which no composition has been applied. Preferably, however, the composition is uniformly applied to the surfaces of the absorbent carrier or to the absorbent surface of the disinfectant article that comprises multiple layers or multiple materials of construction.

Preferably, the composition can be applied to the absorbent carrier at any point after it has been dried. For example, the composition can be applied to the absorbent carrier prior to or after calendaring, and prior to being wound up onto a parent roll. Typically, the application will be carried out on an absorbent carrier unwound from a roll having a width equal to a substantial number of wipes it is intended to produce.

When the absorbent carrier substrate is produced with a bonded liquid impervious layer forming an essentially impervious barrier to one side of the disinfectant article, it is then preferred that application of the disinfectant composition is made to the absorbent side of the article.

Alternatively, the disinfectant composition can also be applied at a later stage in the processing of the disinfectant articles, such as being applied to the substantially dry absorbent carrier after it has been placed into the respective storage pouch, container, canister or other packaging means, but prior to sealing or closure of said packaging means. In this alternative application means, the disinfectant solution is preferably applied by spraying, dripping or nozzle injection of a metered aliquot of the liquid disinfectant composition directly onto the absorbent material within each open package at a convenient processing stage.

The disinfecting composition is typically applied in an amount of from about 1 gram to about 10 gram per gram of absorbent carrier, preferably from about 1.5 gram to about 8.5 gram per gram of absorbent carrier, most preferably from about 2 gram to about 5 gram per gram of dry absorbent carrier. The weight ratio of the disinfecting composition to the absorbent carrier is referred to as the loading ratio and is expressed as a unit-less weight/weight ratio. It is preferred for stability reasons that the loading ratio is greater than 3.0 because this improves the stability of the disinfecting article.

Those skilled in the art will recognize that the exact amount of aqueous composition applied to the absorbent carrier will depend on the basis weight of the absorbent carrier and on the end use of the product. In one preferred embodiment, a relatively low basis weight absorbent carrier, from about 20 g/m² to about 80 g/m², is used in the making of a pre-moistened cleaning and disinfectant wipe suitable for cleaning lightly soiled counters, stove tops, cabinetry, walls, sinks and the like. For such end uses, the dry absorbent carrier is loaded with an aqueous composition of the invention at a factor of from about 2 grams to about 10 grams per gram of dry absorbent carrier. In another preferred embodiment, a higher basis weight absorbent carrier, from about 40 g/m² to about 200 g/m² is used in the making of the pre-moistened disinfectant wipe suitable for cleaning heavily soiled or larger area surfaces, including floors, walls and the like. In such instances, the wipe may further be sold with, or designed to work with, a hand held implement comprising a handle and designed for wiping and cleaning. Examples of such implements are commercially available under the trade names Ready-Mop®, a product of The Clorox Company, and Swiffer®, a product of the Procter and Gamble Company. For such end uses, the dry absorbent carrier is loaded with an aqueous composition of the invention at a factor of from about 2 grams to about 8 grams per gram of dry absorbent carrier.

Disinfectant Actives

Suitable hypohalite compounds may be provided by a variety of sources, including bleaches that lead to the formation of positive halide ions and/or hypohalite ions, as well as bleaches that are organic based sources of halides, such as chloroisocyanurates, haloamines, haloimines, haloimides and haloamides, or mixtures thereof. These bleaches also produce hypohalite-bleaching species in situ. Preferred hypohalite bleaches for use herein include the alkali metal and alkaline earth metal hypochlorites, hypobromites, hypoiodites, chlorinated trisodium phosphate dodecahydrates, potassium and sodium dichloroisocyanurates, potassium and sodium trichlorocyanurates, N-chloroimides, N-chloroamides, N-chlorosulfamide, N-chloroamines, chlorohydantoins, such as dichlorodimethyl hydantoin and chlorobromo dimethylhydantoin, or mixtures thereof.

In a preferred embodiment wherein the compositions herein are liquid, said hypohalite bleach is an alkali metal and/or alkaline earth metal hypochlorite, or mixtures thereof. More preferably, for liquid compositions said hypohalite bleach is an alkali metal and/or alkaline earth metal hypochlorite selected from the group consisting of sodium hypochlorite, potassium hypochlorite, magnesium hypochlorite, lithium hypochlorite and calcium hypochlorite, and mixtures thereof. Even more preferably, for liquid compositions said hypohalite bleach is sodium hypochlorite.

The halogen bleach is preferably present in an amount from above zero (0 ppm) to about 15 weight percent (150,000 ppm) of the composition, and more preferably, from about 0.001 weight percent (10 ppm) to about 10 weight percent (100,000 ppm) of the composition, and most preferably from about 0.01 (100 ppm) to about 1 weight percent (10,000 ppm) of the composition. A particularly preferred bleach in this invention is sodium hypochlorite, having the chemical formula NaOCl, present in an amount ranging from about 0.001 (10 ppm) to about 15 weight percent (150,000 ppm) of the composition, more preferably from about 0.005 (50 ppm) to about 10 weight percent (100,000 ppm), and most preferably from about 0.01 (100 ppm) to about 1 weight percent of the composition.

Electrolyte/Buffer

The electrolyte/buffer component of the cleaning and disinfecting composition promotes a favorable environment of pH and ionic strength in which the hypohalite releasing disinfectant is stabilized against accelerated decomposition and loss of disinfectant efficacy. An electrolyte functions to provide a source of ions (generally anions) in aqueous solution. The electrolyte thus provides a charged medium in which the optional surfactant and/or optional thickeners can associate to provide thickening, or other favorable rheological properties such as shear thinning and/or viscoelastic properties. These properties provide for thickened compositions that may be readily formulated, mixed and handled by commercial processing equipment and effectively transferred by commercial pumping and dosing equipment for convenient loading onto the absorbent carrier. Suitably thickened and rheologically enhanced disinfecting compositions provide the additional benefit of higher loading capabilities onto their respective absorbent carriers, reduced dripping and evaporation during storage and use. Suitably thickened and rheologically enhanced disinfecting compositions also provide the additional benefit of clinging to treated surfaces, particularly uneven, sloped or vertical surfaces with greater tenacity and resistance from gravity to provide more efficient coverage, effective contact time and overall enhancement of the cleaning and disinfectant efficacy of the compositions.

A buffer principally acts to maintain a favorable pH of the associated aqueous disinfectant compositions, particularly when absorbed in intimate contact with the absorbent carrier materials employed. In the present invention, alkaline pH is favored for purposes of maintaining halogen bleach stability. Some compounds will serve as both electrolyte and buffer. These particular electrolyte/buffer compounds are generally various inorganic acids, for example, borates, polyphosphates, pyrophosphates, triphosphates, tetraphosphates, silicates, metasilicates, polysilicates, carbonates, and hydroxides; alkali metal salts of such inorganic acids; and mixtures of same. Certain divalent salts, e.g., alkaline earth salts of phosphates, carbonates, hydroxides, etc., can function singly as buffers. If such a divalent salt compound is used, it is combined with at least one of the above-mentioned electrolyte/buffer compounds to provide the appropriate pH adjustment. It may also be suitable to use materials such as aluminosilicates (zeolites), borates, aluminates and bleach-stable organic materials, such as the lower C1–C10 alkyl dicarboxylic acids including gluconates, succinates, and maleates, as buffers. If necessary, sodium chloride or sodium sulfate can be used as electrolytes, but not buffers, to maintain the ionic strength necessary for the desired rheology, if optional surfactants and/or thickeners are employed.

An especially preferred electrolyte/buffer compound is an alkali metal silicate, which is employed in combination with an alkali metal hydroxide to provide effective pH control and can also function as a metal ion sequestrant. The preferred silicate is sodium silicate, which has the empirical formula $NaO:SiO_2$. The ratio of sodium oxide:silicon dioxide is about 1:4 to 1:1, more preferably about 1:2. Silicates are available from numerous sources, such as the PQ Corporation. The electrolyte/buffer compounds function to keep the pH range of the inventive disinfecting article and composition preferably above 9.0, more preferably at between about 9.5 to about 13.0, and most preferably at between about 10 and 12.

The pH level of the disinfecting article was measured by squeezing out the liquid from the absorbent carrier because this takes into account any influence the absorbent carrier material has on the cleaning composition. The initial pH of the cleaning composition with no contact with an absorbent carrier was measured separately for its independent stability and for comparison purposes. It is preferred that the initial pH of the composition is between about 10 and 13, and more preferably between 11.8 and 12.5. The amount of electrolyte/buffer can vary from about 0.01 to about 10 weight percent of the composition, more preferably from about 0.05 to about 5 weight percent of the composition, and most preferably from about 0.05 to about 1.0 weight percent of the composition.

Water

It should be noted that the main ingredient in the inventive compositions is water, preferably softened, distilled or deionized water. Water provides the continuous liquid phase into which the other ingredients are added to be dissolved/dispersed. The amount of water present generally exceeds 90% and, indeed, can be as high as 99.9%, although generally, it is present in a quantity sufficient (q.s.) to take up the remainder of the specially formulated disinfectant compositions of the present invention.

Surfactant

Optionally, a surfactant suitable for use in this invention is selected from anionic, non-ionic, amphoteric, zwitterionic surfactants and mixtures thereof. It is especially preferred to use a combination of anionic and bleach-stable, non-ionic surfactants. The anionic surfactant is selected from bleach-stable surfactants such as alkali metal alkyl sulfates, secondary alkane sulfonates (also referred to as paraffin sulfonates), alkyl diphenyl ether disulfonates, fatty acid soaps, and mixtures thereof. Such an anionic surfactant will preferably have alkyl groups averaging about 8 to about 20 carbon atoms. In practice, the use of any other anionic surfactant, which does not degrade chemically when in contact with a hypohalite bleaching species, is considered suitable for use in this invention.

An example of a particularly preferred secondary alkane sulfonate is HOSTAPUR SAS, manufactured by Farbwerke Hoechst A.G., Frankfurt, West Germany. Examples of typical alkali metal salts of alkyl benzene sulfonic acids are those manufactured by Pilot Chemical Company sold under the trademark CALSOFT. An example of a typical alkali metal alkyl sulfate is CONCO SULFATE WR, sold by Continental Chemical Company, which has an alkyl group of about 16 carbon atoms. When the electrolyte used is an alkali metal silicate, it is most preferable to include a soluble alkali metal soap of a fatty acid, such as a hexyl to tetradecyl fatty acid soaps. Especially preferred are sodium and potassium soaps of lauric and myristic acid. When used as a component of the inventive cleaning composition, the alkali metal soap of a fatty acid is present in an amount from above zero to about 10 weight percent of the composition.

Examples of preferred bleach-stable, non-ionic surfactants are amine oxides, especially trialkyl amine oxides, as represented in the formula expression RR'R"NO, in which R' and R" may be alkyls of 1 to 3 carbon atoms and are most preferably methyls, and R is an alkyl of about 10 to 20 carbon atoms. When R' and R" are both methyl and R is alkyl averaging about 12 carbon atoms, the structure for dimethyldodecylamine oxide, a particularly preferred amine oxide, is obtained. Representative examples of these particular types of bleach-stable, non-ionic surfactants include the dimethyldodecylamine oxides sold under the trademark AMMONYX LO by Stepan Chemical. Yet other preferred amine oxides are those sold under the trademark BARLOX by Lonza, CONCO XA sold by Continental Chemical Company, AROMAX sold by Akzo, and SCHERCAMOX, sold by Scher Brothers, Inc. These amine oxides preferably have main alkyl chain groups averaging about 10 to about 20 carbon atoms. Other types of suitable surfactants include amphoteric surfactants such as, for example, betaines, imidazolines and certain quaternary phosphonium and tertiary sulfonium compounds.

It is suitable to use one or more surfactants in the inventive compositions. In the inventive composition, total surfactant, when present, is included in an amount ranging from about 0.001 to about 20 weight percent of the composition, preferably in an amount ranging from about 0.01 to about 5 weight percent of the composition. For reduced surface residue and to decrease the tendency of the compositions to contribute to excess foaming, residual filming or streaking, and particularly for use on glossy or shiny surfaces, total surfactant, when present, is included in an amount most preferably from about 0.01 to about 1.0 weight percent of the composition.

Secondary Surfactant

Optionally, an additional co-surfactant may be added to the disinfectant composition of this invention. The bleach stable anionic surfactants include alkali metal alkyl sulfates, alkylarylsulfonates, primary and secondary alkane sulfonates (also referred to as paraffin sulfonates), alkyl diphenyloxide disulfonates, and mixtures thereof. The anionic surfactants have alkyl groups preferably averaging about 8 to 20 carbon atoms. The alkyl arylsulfonic acid salts of preference are linear alkylbenzene sulfonates, known as LAS's. Typical LAS's have C 8–16 alkyl groups, non-limiting examples of which include Stepan Company's Biosoft and Pilot Chemical Company's Calsoft. Still further suitable surfactants are the alkyldiphenylether disulfonates (also called alkyldiphenyloxide disulfonates), such as, by way of example only, those sold by Dow Chemical Company under the name "Dowfax," e.g., Dowfax 3B2. Still other potentially suitable anionic surfactants include alkali metal alkyl sulfates such as Conco Sulfate WR, sold by Continental Chemical Company, which has an alkyl group of about 16 carbon atoms; and secondary alkane sulfonates such as Hostapur SAS, manufactured by Farbwerke Hoechst AG.

Hydrotropes

Hydrotropes, on the other hand, are dispersants, which do not form a critical micelle concentration (CMC) in water (See Colbom, et al, U.S. Pat. No. 4,863,633, column 8, line 20 through column 10, line 22, incorporated herein by reference). These hydrotropes may interact with some of the bleach stable surfactants bearing at least one nitrogen atom to form thickened, viscoelastic formulations. However, it is notable that the thickening phenomenon is not critical to the enhanced brightness retention of the invention. The hydrotropes are preferably selected from short chain alkylarylsulfonates, salts of benzoic acid, benzoic acid derivatives (such as chlorobenzoic acid), and mixtures thereof. As used herein, aryl includes, without limitation, at least benzene, naphthalene, xylene, cumene and similar aromatic nuclei. These aryl groups can be substituted with one or more substituents known to those skilled in the art, e.g., halo (chloro, bromo, iodo, fluoro), nitro, or C 1–4 alkyl or alkoxy. Most preferred is sodium xylene sulfonate (such as Stepanate SXS, available from Stepan Company).

Sequestrant/Chelant

Optionally, sequestering agents are suitable for use in the inventive disinfectant articles. Sequestering agents are selected from the group consisting of metal chelators, metal sequestrants and ion exchange materials known in the art. Preferably, metal chelators and metal sequestrants are selected from the group consisting of the alkali and alkaline earth salts of the phosphates, phosphonates, borates, silicates, polyfunctionally-substituted aromatic chelating agents, ethylenediamine tetra-acetate (EDTA) and ethylenediamine-N,N'-disuccinic acids, or mixtures thereof. Preferred sequestering agents are the silicates and ethylenediamine tetra-acetate.

Polyfunctionally-substituted aromatic chelating agents may also be useful in the bleaching compositions herein. See U.S. Pat. No. 3,812,044, issued May 21, 1974, to Connor et al. Preferred compounds of this type in acid form are dihydroxydisulfobenzenes such as 1,2-dihydroxy-3,-5-disulfobenzene. A preferred biodegradable chelating agent for use herein is ethylene diamine N,N'-disuccinic acid, or alkali metal, or alkaline earth, ammonium or substituted ammonium salts thereof or mixtures thereof.

Sequestering agents are also selected from the group consisting of polyacrylic acid, a polyacrylic acid derivative, or a copolymer of acrylic acid or methacrylic acid and a comonomer, which is maleic acid or maleic anhydride. By "polyacrylic acid derivative" is meant copolymers derived from acrylic monomers and non-acrylic monomers. Acrylic monomers generally refer to esters of acrylic acid and methacrylic acid as well as those of other α-substituted acrylic acids (e.g., α-chloroacrylic, and α-ethylacrylic acids). Preferred acrylic monomers include, for example, acrylic acid and methacrylic acid. Suitable non-acrylic acid monomers include, for example, ethylene and propylene.

Other suitable polycarboxylate sequestering agents include, for example and no by way of limitation, polymethacrylate (DAXAD 30,35,37™ from W. R. Grace & Co. and ALCOSPERSE 124™ from ALCO Chemical), acrylic acid/methacrylic acid (SOKOLAN CP 135™ from BASF Corp.), an oxidized ethylene/acrylic acid, carboxylated vinyl acetate (DARATAK 78L™ from W. R. Grace), vinyl acetate/crotonic acid (LUVISET CA66™ from BASF Corp.), vinyl acetate/vinyl propionate/crontonic (LUVISET CAP™ by BASF Corp.), vinyl acetate/vinyl neodecanoate/crontonic acid (Resyn 28-2930(by National Starch Co.), vinyl acetate/methacryloxy 1-benzophenone/crontonic acid (RESYN 28-3307™ from National Starch Co.), acrylic acid/methylethyl acrylate, ethylene/maleic acid (EMA™ from Monsanto Co.), poly(isobutylene/maleic acid) (DAXAD 31™ from W. R. Grace & Co.), maleic acid/vinyl acetate (LYTRON X 886™ from Monsanto Co.), poly (methyl vinyl ether/maleic acid) (SOKALAN CP2™ from BASF Corp.), poly(styrene/maleic anhydride) and mixtures thereof. Preferably the average molecular weight of the polycarboxylate polymer sequestering agent is between about 500 to about 500,000 daltons and preferably ranges from about 1,000 to about 200,000 daltons, more preferably from about 3,000 to about 70,000 daltons.

Most preferably the sequestering agent is selected from polyacrylic acid, a polyacrylic acid derivative, a copolymer of acrylic acid or methacrylic acid and a comonomer, which is preferably maleic acid or maleic anhydride and mixtures thereof.

Other Adjuncts

The disinfectant composition of the present invention may optionally be formulated to include further adjuncts, for example, thickening agents, rheology modifiers, fragrances, coloring agents, pigments (e.g., ultramarine blue), bleach-stable dyes (e.g., anthraquinone dyes), whiteners, including the optional surfactants, solvents, chelating agents and builders, which enhance performance, stability or aesthetic appeal of the composition. Generally, such adjuncts may be added in relatively low amounts, e.g., each from about 0.001 to about 5.0 weight percent of the composition. By way of example, a fragrance such as a fragrance commercially available from International Flavors and Fragrance, Inc., may be included in the inventive composition in an amount from about 0.01 to about 0.5 weight percent of the composition. Dyes and pigments may be included in small amounts in the composition of the present invention. Examples of widely used, suitable pigments include ultramarine blue (UMB) and copper phthalocyanines.

Solvents may also be added to the inventive compositions to enhance cleaning and/or disinfectant efficacy of the compositions. For example, certain less water soluble or dispersible organic solvents, some of which are advantageously stable in the presence of hypochlorite bleach, may be included. These bleach-stable solvents include those commonly used as constituents of proprietary fragrance blends, such as terpenes and essential oils, and their respective derivatives.

The terpene derivatives suitable for the present invention include terpene hydrocarbons with a functional group. Effective terpenes with a functional group include, but are not limited to, alcohols, ethers, esters, aldehydes and ketones. Representative examples of each of the above-mentioned terpenes with a functional group include, but are not limited to, the following: (1) terpene alcohols, including, for example, verbenol, transpinocarveol, cis-2-pinanol, nopol, iso-borneol, carbeol, piperitol, thymol, alpha-terpineol, terpinen-4-ol, menthol, 1,8-terpin, dihydroterpineol, nerol, geraniol, linalool, citronellol, hydroxycitronellol, 3,7-dimethyl octanol, dihydromyrcenol, beta-terpineol, tetrahydro-alloocimenol and perillalcohol; (2) terpene ethers and esters, including, for example, 1,8-cineole, 1,4-cineole, iso-bomyl methylether, rose pyran, alpha-terpinyl methyl ether, menthofuran, trans-anethole, methyl chavicol, allocimene diepoxide, limonene mono-epoxide, iso-bornyl acetate, nopyl acetate, alpha-terpinyl acetate, linalyl acetate, geranyl acetate, citronellyl acetate, dihydro-terpinyl acetate and neryl acetate; and (3) terpene aldehydes and ketones, including, for example, myrtenal, campholenic aldehyde, perillaldehyde, citronellal, citral, hydroxy citronellal, camphor, verbenone, carvenone, dihydrocarvone, carvone, piperitone, menthone, geranyl acetone, pseudo-ionone, alpha-ionone, beta-ionone, iso-pseudo-methyl ionone, normal-pseudo-methyl ionone, iso-methyl ionone and normal-methyl ionone. Terpene hydrocarbons with functional groups which appear suitable for use in the present invention are discussed in substantially greater detail by Simonsen and Ross, The Terpenes, Volumes I–V, Cambridge University Press, $2^{nd}$ Ed., 1947, which is incorporated herein in entirety by this reference. See also, commonly assigned U.S. Pat. No. 5,279, 758, issued to Choy on Jan. 18, 1994, which is incorporated herein in entirety by this reference.

Housing Systems and Packaging Materials

Suitable packaging materials may be provided by a variety of sources, and include all suitable materials that are hypohalite stable, in that they undergo no significant degradation. That is, the packaging materials undergo no significant chemical or physical change in structure, properties or form, owing to contact with the hypohalite compositions employed in the present invention. Suitable packaging materials include those materials common to the art.

Housing systems include both individually packaged disinfectant wipes and bulk packaged one or more disinfectant wipes or other suitable disinfecting articles. The housing system preferably comprises a sealable container, which is substantially impervious to both liquid and gas. The term "container", refers to, but is not limited to, packets containing one or more individual disinfectant wipes and bulk dispensers, such as canisters, tubs and jars, which dispense one disinfectant wipe at a time, and further feature suitable means to reseal the bulk dispenser between uses to preserve the integrity of the disinfecting articles. One example is a cylindrical canister dispenser that hosts a roll of individual wipes, separated by perforations to permit the tearing off of individual wipes for use. Such dispenser is conveniently gripped by the user and held in position while the user removes a wipe. Preferred are dispensers featuring a resealable dispensing cap and orifice (See, e.g., Chong, U.S. Pat. No. 6,554,156, of common assignment and incorporated herein by reference thereto) that dispenses individual wipes from a roll and retains the next wipe in a ready-to-dispense position, yet allows sealing of the dispensing cap to close the container against the environment when not in use. A further example, within the scope of the present invention, is to package individual wipes in a non-linked manner, in a dispenser permitting their removal one at a time, as is the case with many wipe/dispenser combinations known in the art.

Experimental Results

TABLE 1

Stability Testing Using pH Levels and Expected Consumer Behavior

| Number of Days | pH level for wipes stored at 70° F. | pH level for wipes stored at 100° F. | pH level for wipes stored at 120° F. |
|---|---|---|---|
| 0 | 11.8 | 11.8 | 11.8 |
| 4 | 11.75 | 11.73 | 10.74 |
| 5 | 11.15 | 10.57 | 10.17 |
| 6 | 11.56 | 10.96 | 10.34 |
| 11 | 11.64 | 10.95 | 10.11 |
| 13 | 11.59 | 10.83 | 10.10 |
| 18 | 10.68 | 10.67 | 9.80 |
| 20 | 10.06 | 10.43 | 9.56 |
| 22 | 10.77 | 10.35 | 9.66 |

The disinfectant wipes for this stability test contained about 0.6% NaOCl, 0.015% NaOH, 0.03% fragrance, 0.55% Ammonyx DO, 0.15% SXS, and 0.5% Silicate N on a PET substrate. During the course of the stability test, the results of which are in table 1, 9 wipes were pulled and tested from each sealable cylindrical container. The containers hold a roll of wipes and have an orifice for dispensing wipes individually. The testing of the three containers was performed over the period of 22 days where each canister was stored at controlled temperatures of 70° F., 100° F. and 120° F. These temperatures were intended to replicate different types of consumer use and test long-term stability. The testing was performed by squeezing the liquid from the disinfecting wipes to measure the pH. The pH levels of the 70° F. articles were overall higher than those of the 100° F. articles, which in turn had higher pH levels than the 120° F. article. Each of the samples showed a substantial drop in pH levels around the 4$^{th}$ day and then pH levels increased a little before they began to decrease more steadily over time. Acceleration calculations done with this data indicated that the stability and effectiveness of the wipes could be maintained for about a year at 70° F.

TABLE 2

Effect of Buffer Type on Stability of PET Wipe

| | Number of Days | | | | |
|---|---|---|---|---|---|
| | 0 | 14 | 21 | 28 | 35 |
| % NaOCl for NaOH only | 0.59 | 0 | 0 | 0 | 0 |
| % NaOCl for 0.5% Silicate N, pH = 11.59 | 0.59 | 0.49 | 0.46 | 0.38 | 0.24 |
| % NaOCl for 0.5% Silicate N, pH = 12.44 | 0.63 | 0.45 | 0.41 | 0.35 | 0.21 |
| % NaOCl for 0.5% Silicate N, pH = 12.89 | 0.63 | 0.47 | 0.31 | 0.21 | 0.06 |
| % NaOCl for 0.015% Silicate N +0.005% Na$_3$PO$_4$ | 0.59 | 0.58 | 0.58 | 0.51 | 0.005 |
| % NaOCl for 0.5% Na$_3$PO$_4$, pH = 12.45 | 0.66 | 0.53 | 0.36 | 0.11 | 0 |
| % NaOCl for 0.5% Borate, pH = 12.41 | 0.64 | 0 | 0 | 0 | 0 |
| % NaOCl for 0.5% Na$_2$CO$_3$, pH = 12.44 | 0.63 | 0.45 | 0 | 0 | 0 |

To perform a stability test on the effect of buffer type, the results of which are shown in Table 2, each buffer sample was put on a PET substrate that contained about 0.6% NaOCl, 0.015% NaOH, 0.03% fragrance, 0.55% Ammonyx DO, 0.15% SXS, and 0.5% Silicate N. The test was performed over the period of 28 days in a 120° F. controlled temperature room. The testing was performed by squeezing the liquid from the disinfecting wipes to measure the remaining percentage of NaOCl. The disinfecting articles were evaluated for activity using oxidation/reduction titration methods known to those in the art to determine the percentage of remaining sodium hypochlorite. The results indicate the NaOH only and 0.5% Borate samples were the least stable and after 14 days because neither one had a significant amount of sodium hypochlorite remaining. The carbonate and phosphate samples demonstrated good stability until approximately the 14$^{th}$ day and then the level of NaOCl began to decrease dramatically. Unlike the other buffer samples, the 0.5% Silicate N samples showed a steady decline in the percentage of NaOCl over time, but the overall percentage of NaOCl remained substantially higher than the other buffer samples at the end of the 28-day period, which correlates to a higher level of stability and efficacy for the disinfecting articles.

TABLE 3

The Effect of the Loading Ratio on PET Wipe Stability Using pH

| | Number of Days | | | | |
|---|---|---|---|---|---|
| | 0 | 7 | 14 | 21 | 28 |
| % NaOCl for 3.0 Loading Ratio | 0.69 | 0.66 | 0.52 | 0.37 | 0.17 |
| % NaOCl for 3.5 Loading Ratio | 0.69 | 0.66 | 0.53 | 0.41 | 0.17 |
| % NaOCl for 4.5 Loading Ratio | 0.69 | 0.66 | 0.56 | 0.46 | 0.26 |
| Sample without PET substrate | 0.69 | 0.68 | 0.65 | 0.63 | 0.61 |

As shown in Table 3, the disinfectant articles for the loading ratio test contained about 0.69% NaOCl, 0.015% NaOH, 0.03% fragrance, 0.55% Ammonyx DO, 0.15% SXS, and 0.5% Silicate N on a PET substrate. The loading test was performed at a controlled temperature of 120° F. The test samples were obtained by squeezing the liquid from the disinfecting wipes to measure the remaining percentage of NaOCl. The disinfecting articles were evaluated for activity using oxidation/reduction titration methods known to those in the art to determine the percentage of remaining sodium hypochlorite. The table shows that a higher loading ratio improves the stability of the disinfecting substrate slightly over the course of 28 days. This increase in 28-day stability correlates to a much more dramatic increase in stability over the course of an entire year.

TABLE 4

Fiber's Denier Size Effect on Stability

| | Number of Days | | | | |
|---|---|---|---|---|---|
| | 0 | 7 | 14 | 21 | 28 |
| pH level of 100% PET 1D fibers DuPont 8090 | 11.90 | 11.64 | 11.50 | 11.43 | 11.38 |
| pH level of 100% PP 1.5D fibers DuPont T133 | 11.90 | 11.65 | 11.52 | 11.48 | 11.42 |
| pH level of 100% PPWA[a] 4D fibers from FiberVisions | 11.90 | 11.71 | 11.69 | 11.66 | 11.61 |
| PH level of 100% PPWA 6D fibers from FiberVisions | 11.90 | 11.73 | 11.71 | 11.65 | 11.62 |

[a]hydrophilically modified PP with hypochlorite stable wetting agent

As shown in Table 4, the disinfectant articles for the denier size stability test contained about 0.6% NaOCl, 0.015% NaOH, 0.03% fragrance, 0.55% Ammonyx DO, 0.15% SXS, and 0.5% Silicate N. The testing was performed at a controlled temperature of 100° F. over the course of 28 days. The larger denier PP fibers, 1.5 denier or higher, are more effective at maintaining pH levels and have better stability than the standard denier size fibers.

TABLE 5

Substrate Type Effect on Stability

| | Number of Days | | | | |
|---|---|---|---|---|---|
| | 0 | 7 | 14 | 21 | 28 |
| pH level of 100% PET 8090 N Silicate 0.5% | 11.90 | 11.11 | 10.81 | 10.44 | 10.05 |
| pH level of 100% PP T133 N Silicate 0.5% | 11.90 | 11.77 | 11.42 | 11.27 | 10.84 |
| pH level of 80% PP/20% PET 89D Metasilicate 0.5% | 12.50 | 12.22 | 12.04 | 11.69 | 11.41 |
| pH level of 50% PP/50% PET 89C Metasilicate 0.5% | 12.50 | 12.09 | 11.77 | 11.34 | 11.02 |

The disinfectant wipes for substrate testing, the results of which are shown in Table 5, contained about 0.6% NaOCl, 0.015% NaOH, 0.03% fragrance, 0.55% Ammonyx DO and 0.15% SXS. The testing was performed in at a controlled temperature of 100° F. The data indicates that the 100% PP wipe was able to maintain a higher pH level than the 100% PET wipe over the span of 28 days. Since PP is less absorbent than PET, blends of PP and PET were tested to see if the substrate absorbency could be increased while maintaining high pH levels. The results indicate that blends of PP and PET are significantly more stable at higher pH levels than either PP or PET alone. The 80% PP and 20% PET wipe showed the best results and was noticeably more stable than the 50% PP and 50% PET wipe.

The testing methods described are not intended to limit in any manner the scope or equivalents to which the invention is entitled, the invention is further characterized by the claims, which follow.

What is claimed is:

1. A disinfecting article comprising:
   a. an aqueous hypohalite releasing composition; and
   b. an absorbent carrier containing said aqueous hypohalite releasing composition;
   c. wherein said absorbent carrier comprises fibers having a denier of 1.5 or greater; and
   d. wherein the loading ratio of the aqueous hypohalite releasing composition to the absorbent carrier is greater than 3.

2. The disinfecting article of claim 1, wherein said absorbent carrier comprises fibers having a denier of 3.0 or greater.

3. The disinfecting article of claim 1, wherein said absorbent carrier further comprises apertures.

4. The disinfecting article of claim 1, wherein said absorbent carrier comprises fibers selected from the group consisting of polyester, polypropylene, polyethylene, hydrophilically modified polyester, hydrophobically modified polyester, hydrophilically modified polypropylene, hydrophilically modified polyethylene and mixtures thereof.

5. The disinfecting article of claim 4, wherein said absorbent carrier comprises polyester fibers.

6. The disinfecting article of claim 4, wherein said absorbent carrier comprises hydrophilically modified polypropylene fibers.

7. The disinfecting composition of claim 1, wherein said aqueous hypohalite releasing composition comprises a buffering system selected from the group consisting of a an alkali metal phosphate, an alkali metal silicate, an alkali metal hydroxide, and mixtures thereof.

8. The disinfecting composition of claim 1, wherein said aqueous hypohalite releasing composition comprises a buffering system comprising a mixture of an alkali metal phosphate and an alkali metal silicate.

9. The disinfecting article of claim 1, wherein said absorbent carrier further comprises at least one layer of liquid impervious barrier material.

10. The disinfecting article of claim 1, wherein said disinfecting article attaches to a cleaning implement.

11. A disinfecting article comprising:
   a. an aqueous hypohalite releasing composition comprising a surfactant; and
   b. an absorbent carrier containing said aqueous hypohalite releasing composition;
   c. wherein said aqueous hypohalite releasing composition comprises a buffering system selected from the group consisting of an alkali metal phosphate, an alkali metal silicate, an alkali metal hydroxide, and mixtures thereof;
   d. wherein the loading ratio of the aqueous hypohalite releasing composition to the absorbent carrier is greater than 3: and
   e. wherein said absorbent carrier comprises fibers selected from the group consisting of polyester, polypropylene, polyethylene, hydrophilically modified polyester, hydrophobically modified polyester, hydrophilically modified polypropylene, hydrophilically modified polyethylene and mixtures thereof.

12. The disinfecting article of claim 11, wherein said aqueous hypohalite releasing composition has a pH of at least 10.

13. The disinfecting article of claim 11, wherein said aqueous hypohalite releasing composition has a pH of at least 11.

14. The disinfecting article of claim 11, wherein said aqueous hypohalite releasing composition has a pH between 11.5 and 12.5.

15. The disinfecting article of claim 11, wherein the loading ratio of the aqueous hypohalite releasing composition to the absorbent carrier is at least 3.5.

16. The disinfecting article of claim 11, wherein said absorbent carrier comprises apertures.

17. The disinfecting article of claim 11, wherein said absorbent carrier comprises polyester fibers.

18. The disinfecting article of claim 11, wherein said absorbent carder comprises hydrophilically modified polypropylene fibers.

19. The disinfecting article of claim 11, wherein said aqueous hypohalite releasing composition comprises a buffering system selected from the group consisting of, an alkali metal silicate, an alkali metal hydroxide, and mixtures thereof.

20. The disinfecting article of claim 11, wherein said aqueous hypohalite releasing composition comprises a buffering system comprising a mixture of an alkali metal phosphate and an alkali metal silicate.

21. The disinfecting article of claim 11, wherein said absorbent carrier further comprises at least one layer of liquid impervious barrier material.

22. The disinfecting article of claim 11, wherein said aqueous hypohalite releasing composition is sodium hypochlorite.

23. The disinfecting article of claim 11, wherein the composition further comprises a fragrance.

24. The disinfecting article of claim 11, wherein said disinfecting article attaches to a cleaning implement.

* * * * *